(12) United States Patent
Ryu et al.

(10) Patent No.: US 7,319,176 B2
(45) Date of Patent: Jan. 15, 2008

(54) SELECTIVE HYDROGENATION OF ACETYLENES

(75) Inventors: J. Yong Ryu, Houston, TX (US); John R. Adams, Houston, TX (US); Willibrord A. Groten, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 357 days.

(21) Appl. No.: 11/010,907

(22) Filed: Dec. 13, 2004

(65) Prior Publication Data

US 2005/0154241 A1 Jul. 14, 2005

Related U.S. Application Data

(63) Continuation of application No. 10/215,096, filed on Aug. 8, 2002, now abandoned.

(51) Int. Cl.
*C07C 7/163* (2006.01)

(52) U.S. Cl. ............ 585/265; 585/258; 585/261; 585/260

(58) Field of Classification Search ......... 585/258, 585/261, 260
See application file for complete search history.

(56) References Cited

U.S. PATENT DOCUMENTS

| | | | | |
|---|---|---|---|---|
| 3,205,281 | A | 9/1965 | Fleming et al. | 260/683 |
| 3,691,248 | A | 9/1972 | Ffrench | 260/677 |
| 3,793,388 | A | 2/1974 | Pitzer et al. | 260/677 |
| 3,897,511 | A | 7/1975 | Frevel et al. | 260/681 |
| 4,440,956 | A | 4/1984 | Couvillion | 585/260 |
| 4,469,907 | A | 9/1984 | Araki et al. | 585/259 |
| 4,493,906 | A | 1/1985 | Couvillion | 502/346 |
| 4,504,593 | A | 3/1985 | Trinh Dinh et al. | 502/154 |
| 4,831,200 | A | 5/1989 | Debras et al. | |
| 5,595,634 | A | 1/1997 | Hearn et al. | 203/29 |
| 5,866,734 | A | 2/1999 | Flick et al. | 585/260 |
| 5,877,363 | A | 3/1999 | Gildert et al. | |
| 6,169,218 | B1 | 1/2001 | Hearn et al. | |
| 6,413,413 | B1 | 7/2002 | Smith, Jr. | |
| 6,414,205 | B1 | 7/2002 | Stanley et al. | |
| 6,576,588 | B2 | 6/2003 | Ryu et al. | |
| 6,717,022 | B2 | 4/2004 | Ryu et al. | |
| 6,734,328 | B1 | 5/2004 | Ryu | |
| 6,867,338 | B2 | 3/2005 | Gelbein et al. | |
| 7,022,645 | B2 | 4/2006 | Ryu et al. | |
| 7,041,860 | B2 | 5/2006 | Ryu | |
| 7,045,669 | B2 | 5/2006 | Sumner et al. | |
| 7,196,035 | B2 | 3/2007 | Ryu et al. | |
| 7,208,646 | B2 | 4/2007 | Boyer | |

FOREIGN PATENT DOCUMENTS

GB 1182929 4/1970

OTHER PUBLICATIONS

Non Final Office Action issued in U.S. Appl. No. 10/828,823, filed May 16, 2007.
Final Office Action issued in U.S. Appl. No. 10/912,252, filed Jul. 7, 2005.
Non Final Office Action issued in U.S. Appl. No. 11/171,797, filed Aug. 4, 2006.

*Primary Examiner*—Thuan Dinh Dang
(74) *Attorney, Agent, or Firm*—Osha Liang LLP

(57) ABSTRACT

A process for removing acetylenic compounds using unsulfided metallic nickel or unsulfided metallic nickel modified with metallic Mo, Re, Bi or mixtures in which the catalyst is used alone or is used in combination with other acetylenic selective catalysts. The unsulfided metallic nickel catalyst or modified catalyst must be the first catalyst to contact the hydrocarbon stream.

19 Claims, 10 Drawing Sheets

Fig. 7 Example 5

Fig. 8 Example 5

Fig. 9  Example 6

SELECTIVE HYDROGENATION OF ACETYLENES

BACKGROUND OF THE INVENTION

This is a continuation of application Ser. No. 10/215,096 filed on Aug. 8, 2002, now abandoned.

1. Field of the Invention

The present relates to the removal of acetylenic compounds from olefin containing streams, in particular streams containing diolefins.

2. Related information

The crude streams for the commercial production of olefins and dienes contain various compounds as impurities. Acetylenic impurities need to be removed from the streams to produce acceptable quality olefin and diene products. A preferred technique for removing the acetylenic impurities is partial hydrogenation, often called selective hydrogenation. For the commercial production of olefins and dienes, the catalytic hydrogenation of acetylenic compounds is utilized to remove acetylenic impurities in the crude product stream.

To produce olefins such as ethylene, propylene, butadiene, isoprene and the like, acetylenic impurities such as acetylene, methyl acetylene, vinyl acetylene, ethyl acetylene, 2-methyl-1-buten-3-yne and the like, in various crude mixed $C_2$-$C_5$ streams need to be removed with minimum loss of useful materials such as ethylene, propylene, butenes, butadiene, isoprene and the like in the feed streams. The preferred technique for the purification in commercial practice is the selective hydrogenation of acetylenic compounds over hydrogenation catalysts.

The difficulty in the catalytic hydrogenation of acetylenic compounds rises from the fact that the hydrogenation must be carried out in the presence of a large excess of olefins or dienes or both. Under the industrial conditions, valuable olefin and diene products in the crude product streams are not inert. This is especially true as the conversion of acetylenic compounds approaches completion, resulting in the loss of valuable products. Therefore, during the selective hydrogenation of acetylenic compounds, minimizing the loss of olefins and dienes is highly desirable for the commercial production of olefins such as ethylene, propylene, and styrene and dienes such as 1,3-butadiene and isoprene. The selectivity of a catalyst is often the determining factor in selecting a catalyst for the production of olefins and dienes.

Acetylenic compounds have been hydrogenated over all Group VIII metals and copper catalysts. Specifically catalytic partial hydrogenation of acetylenic compounds to olefinic compounds which are important for industrial production of olefins, dienes and fine chemicals. All Group VIII metals (Pd, Pt, Rh, Ru, Ir and Os) and non noble metals (Fe, Co and Ni), and Cu catalysts have been known to be active for the hydrogenation of acetylenic compounds and olefins. All Group VIII noble metal catalysts and Ni catalysts have satisfactory catalytic activities for application in the commercial hydrogenation process. But more important for a catalyst is the selectivity for the hydrogenation of acetylenic compounds because of over hydrogenation of olefinic compounds during hydrogenation of acetylenic compounds.

The difficulty of hydrogenating an acetylenic group in a molecule depends on the location of the triple bond on the molecule whether there is conjugation or an olefin group. An isolated terminal triple bond is easiest to selectively hydrogenate. Conjugated triple bond with double bond is much more difficult for the selective hydrogenation. In the study on the hydrogenation of acetylene, methyl acetylene, and dimethyl acetylene (G. C. Bond et al., J. Catalysis 174, 1962), it is reported that the order of decreasing selectivity is Pd>Rh>Pt>Ru>Os>Ir. L. Kh. Freidlin et al., Dokl. Akad. Nauk SSSR 152 (6), 1383, 1962 reported that the order is palladium black>platinum black>rhodium black>Raney nickel>Raney cobalt for the terminal acetylenes and palladium black>Raney nickel>platinum black>Raney cobalt>rhodium black for internal acetylenes. Palladium on barium sulfate is reported to be more selective than Raney nickel in hydrogenation of vinyl acetylene in liquid phase (Catalytic Hydrogenation over Platinum Metals by Paul. N. Rylander, p.75, Academic Press, 1967). Product analysis at 100% conversion of vinyl acetylene indicates that the product from Raney nickel catalyst contains only about half the butadiene (35%) and 23 times the butane (23%) compared with the product from palladium supported on barium sulfate.

Supported Pd, Ni, Cu and Co catalysts have been known to be useful for the hydrogenation of acetylenes (Handbook of Commercial Catalysts, pp. 105-138, Howard F. Rase, CRC Press, 2000). The most preferred catalysts in commercial application of selective hydrogenation of acetylenes are palladium-based catalysts such as Pd, Pd/Pb, Pd/Ag or Pd/Au on a support such as alumina and the copper catalyst on a support such as alumina. Pd catalysts are the most preferred catalysts because of high activity and supposedly superior selectivity compared with other metal catalysts.

The prior art widely demonstrates that palladium catalysts have the highest selectivity for the selective hydrogenation of acetylenes among Group VIII metals. No art has been found showing higher selectivity of nickel catalysts over palladium catalysts. In fact, palladium catalysts are the choice of all current commercial processes for the selective hydrogenation of acetylenic impurities (vinyl acetylene, ethyl acetylene and methyl acetylene) in the crude butadiene streams and crude $C_3$ olefin streams.

1,3-Butadiene is an important raw material for production of various polymers such as butadiene-styrene copolymer. One of the processes for producing 1,3-butadiene is co-production of various olefins by steam cracking of petroleum fractions. The crude mixed $C_4$ stream from a steam cracker is selectively hydrogenated to partially remove $C_4$ acetylenic compounds. The selectively hydrogenated stream is sent to the 1,3-butadiene recovery unit where solvent extractive distillation is used to separate 1,3-butadiene from the rest of components in the mixed stream. Complete removal of $C_4$ acetylenic compounds in the stream with high recovery of 1,3-butadiene is highly desirable to reduce the production cost of 1,3-butadiene and produce premium quality product for polymer production. Heretofore, it was technically impossible to completely remove $C_4$ acetylenes in crude mixed streams by selective hydrogenation without an unacceptably high loss of 1,3-butadiene due to over hydrogenation of 1,3-butadiene. Therefore, an improved inexpensive process via highly active and selective catalysts is highly desirable to produce premium quality 1,3-butadiene without paying a penalty for high loss of 1,3-butadiene due to over hydrogenation.

The palladium-based catalysts for selective hydrogenation of $C_4$ acetylenic compounds are highly active. However, their level of selectivity does not allow complete removal of $C_4$ acetylenes without an unacceptable high loss of 1,3-butadiene due to over hydrogenation. Another inherent problem of palladium-based catalysts is the loss and migration of palladium due to the formation of soluble Pd complex compound by the reaction of Pd atoms on the catalyst surface with vinyl acetylene, if the hydrogenation is carried out in the presence of a liquid phase. Silver and gold have been used to minimize the loss of palladium and reduce catalytic polymerization of acetylenic compounds. Palladium-based catalysts are disclosed in U.S. Pat. No. 5,877,363 (1999), and EP 0 089 252 (1983). U.S. Pat. No. 5,877,363 (1999) disclosed the process for the selective hydrogenation of acetylenic impurities and 1,2-butadiene in mixed olefin rich $C_4$ streams by using supported Pt and Pd catalysts.

The copper-based catalyst is very selective so that the recovery of 1,3-butadiene from the mixed stream is higher than palladium-based catalysts. However, since the activity of copper catalysts is very low compared with palladium-based catalysts, a large volume of catalyst and large reactor are required. The copper catalyst cokes up quickly and frequent regeneration of the catalyst is necessary. Such catalysts are disclosed in U.S. Pat. No. 4,440,956 (1984) and U.S. Pat. No. 4,494,906 (1985).

In the present research it was found that the selective hydrogenation of $C_3$ and $C_4$ acetylenic compounds in a crude butadiene stream over a supported commercial Pd (0.2 wt. %)-Ag (0.1 wt. %) catalyst decreases as the hydrogenation temperature increases; an effect also noted by H. Uygur et al. in liquid phase selective hydrogenation of methyl acetylene/propadiene (MAPD) in a mixed $C_3$ stream (J. Chem. Eng. Japan, 31, p. 178, 1998). This seemingly strange behavior is attributed to a combined effect of very low activation energy (<0.5 kcal.mole) of the selective hydrogenation in liquid phase, higher hydrogen solubility in the feed stream at lower temperature, and temperature dependency of adsorption of acetylenic compounds on palladium surface in ternary phase reaction system of gas, liquid and solid catalyst. The concentration of hydrogen in the liquid phase is more influential on the selective hydrogenation rate of acetylenic compounds than the effect of activation energy.

According to R. S. Mann et al. (Can. J. Chem. 46, p. 623, 1968), Ni and Ni—Cu alloy catalysts are effective for methyl acetylene hydrogenation. The catalytic activity rapidly increases with addition of copper to nickel up to 25 wt. % in alloy catalyst. The selectivity to propylene and extent of polymerization increase with increasing of copper in the alloy.

According to H. Gutmann and H. Lindlar (Organic Synthesis, Chapter 6), vinyl acetylene and 2-methyl-1-buten-3-yne are difficult to selectively hydrogenate to 1,3-butadiene and isoprene by using the usual palladium, nickel or cobalt catalysts. But the palladium catalyst supported on calcium carbonate treated with mercury acetate is useful for the selective hydrogenation.

Nickel-based catalysts are known in the art to be effective for the selective hydrogenation of acetylenic impurities in mixed streams of olefins. It is well documented that nickel catalysts in any form are highly active for hydrogenation of olefins and benzene. Because of very high activity of Ni catalysts for hydrogenation of olefins, the selective hydrogenation of acetylenes in mixtures of dienes or olefins is preferentially carried out over the presulfided nickel catalyst or in the presence of moderating agent for the nickel catalysts, as known in the prior art.

There is no disclosure of selective hydrogenation of $C_4$ acetylenes in crude butadiene streams in the presence of a supported nickel metal catalyst in unsulfided form as equal or superior to the palladium-based catalyst. Nickel catalysts are disclosed in U.S. Pat. No. 4,504,593 (1985) and U.S. Pat. No. 3,691,248 (1972).

U.S. Pat. No. 4,504,593 teaches the use of supported bimetallic catalyst comprised of at least one group VIII metal selected from the Pt, Pd, Ni and Co group, and at least one metal from the Ge, Sn, and Pb group for selective hydrogenation of acetylenic hydrocarbons and diolefins in the olefinic mixtures to mono-olefins. The catalyst contains 0.1 to 10 wt. % Ni, preferably from 1 to 5 wt. %, on a support such as alumina (70 $m^2$/g and 0.5 cc/g total pore volume). The catalysts are prepared in two steps, introducing the second component (Ge, Sn or Pb) of the catalyst to the Ni catalyst from the first step. The selective hydrogenation is preferably carried out in the presence of sulfur and nitrogen compound to obtain acceptable improved selectivity. However, the patent does not suggest the selective hydrogenation of $C_4$ acetylenes in mixed butadiene streams in the absence of sulfur with the activated Ni metal catalyst.

U.S. Pat. No. 3,793,388 (1974) disclosed the selective hydrogenation of acetylene in olefin mixtures in the presence of nickel catalyst supported on alumina. The alumina is characterized by having a substantial portion of pores having at least 120 Å diameter and at least 2 $m^2$/g surface area. The nickel content on the catalyst is from about 0.5 to about 8 mg per square meter of total alumina surface area.

Br 1,182,929 (1970) disclosed a useful catalyst for selective hydrogenation of acetylenic hydrocarbons in an olefin mixture such as crude butadiene stream. The catalyst is the nickel promoted copper catalyst supported on a carrier. The weight of the copper component on the catalyst exceeds the weight of Ni and the weight of the carrier exceeds the weight of active metal components. The final catalyst in mixed oxide form is prepared by calcining a mixture of oxides at 850° C. The catalyst is activated by reducing at a temperature from 180° to 600° C. with a hydrogen-containing gas. The metallic active components on the activated catalyst is at least 25% by weight of the active metal components. The remaining percentage is in the form of their oxides. The selective hydrogenation is carried out in gas phase at a temperature from 100° to 250° C. and about 1 WHSV. The cycle time is about 420 hours.

U.S. Pat. No. 4,748,290 (1988) disclosed a nickel boride catalyst supported on alumina for hydrogenation of acetylenic and diolefinic compounds to monoolefinic compound. Reacting supported nickel arsenate with a borohydride compound activates the catalyst.

U.S. Pat. No. 4,831,200 (1989) disclosed the process for a two-step selective hydrogenation of acetylenic impurities in crude butadiene stream. The acetylenic impurities in crude feed streams are partially hydrogenated in the palladium-based catalyst disclosed in U.S. Pat. No. 4,533,779 and then the remaining impurities are hydrogenated in the copper-base catalyst disclosed in U.S. Pat. Nos. 4,493,906 and 4,440,956 discussed above.

The present process has as an advantage of a greater selectivity for the removal of acetylenic compounds from hydrocarbon streams with higher yields of the desired olefinic compounds. In particular, the present process provides a higher yield of 1,3-butadiene of higher purity from crude $C_4$ streams. It is a particular feature of the present invention that it employs an inexpensive and readily available catalyst at key points in the process which leads to a further advantage that other sulfur or heavy metal sensitive catalysts such as the palladium and copper-based catalysts may also be employed down stream for further improvements. These and other advantages and features of the present invention will become apparent from the following disclosures.

SUMMARY OF THE INVENTION

Briefly, the present invention is a process for removing acetylenic compounds from hydrocarbon streams, comprising contacting hydrogen and a hydrocarbon stream containing acetylenic compounds with a catalyst comprising a supported unsulfided metallic nickel catalyst under hydrogenation conditions to selectively hydrogenate a portion of said acetylenic compounds. In addition to unsulfided nickel metal the catalyst may contain the metals of Mo, Re, and/or Bi. The unsulfided nickel metal comprises the major portion of the metal components on the support.

DETAILED DESCRIPTION

Figure 1:
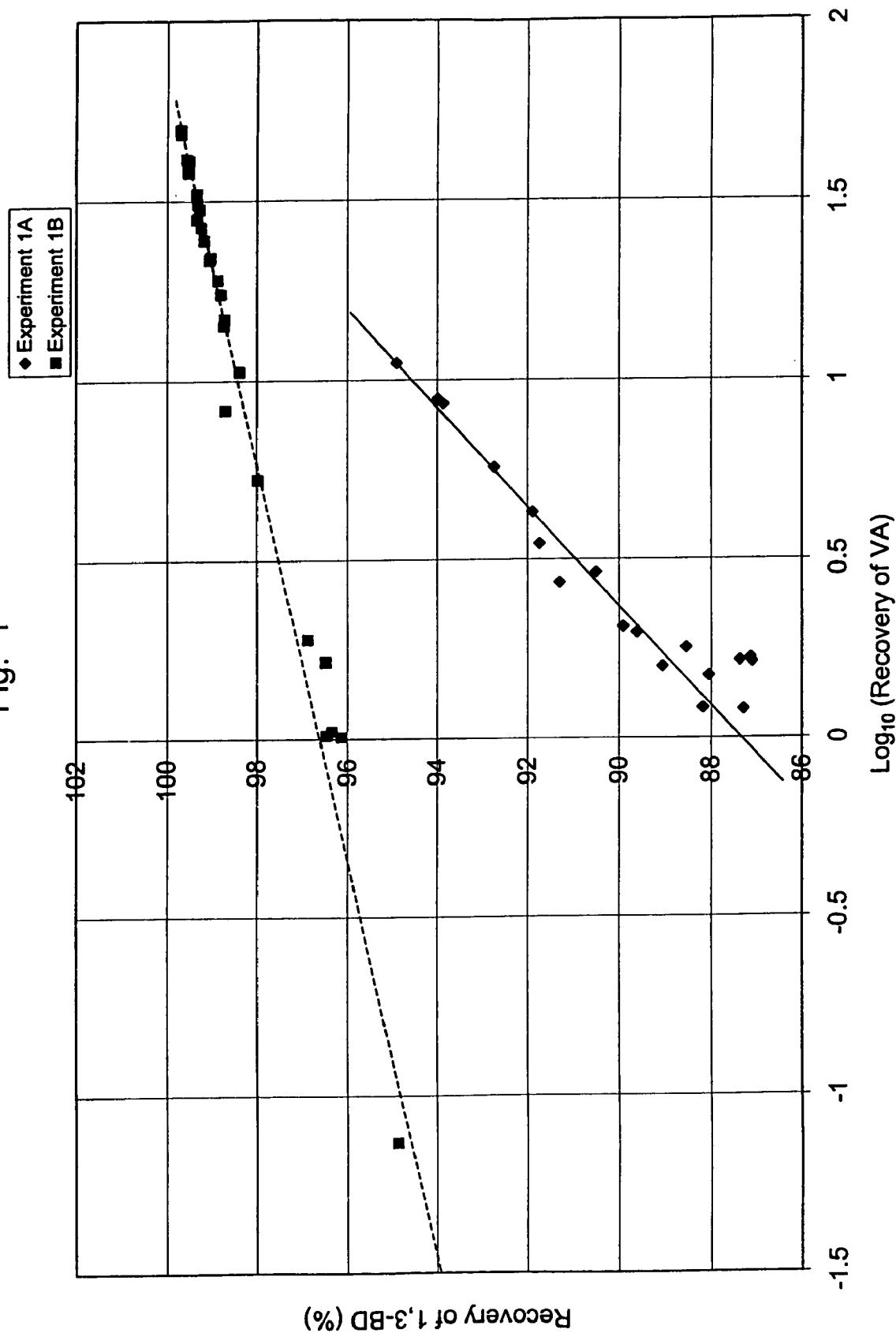
FIG. 1 is a chart comparing Examples 1A and 1B for vinyl acetylene removal.

It has been found during the development of the present invention that unsulfided nickel catalysts surprisingly have higher selectivity than palladium catalyst for acetylenic compounds. In addition, unsulfided nickel catalysts have other highly desirable properties for the selective hydrogenation of C4 acetylenes compared to palladium catalysts for production of 1,3-butadiene. Acetylenic impurities in various mixed streams comprising $C_2$-$C_{12}$ olefins, diolefins and styrene are removed by selective hydrogenation. The selective hydrogenation is performed by passing the feed through either a single catalytic reaction zone or multiple catalytic reaction zones, depending on the nature of feed and the objective of the process. It was discovered that the nickel-based catalyst in unsulfided form is surprisingly the more effective for the selective hydrogenation of acetylenic impurities such as vinyl acetylene, ethyl acetylene, and the like, and results in the least over hydrogenation of dienes such as 1,3-butadiene than the most commercially favored palladium-based catalysts. It is important that the active metallic nickel-based catalyst must not be presulfided or contain arsenic prior to the selective hydrogenation to obtain the superior performance compared to the prior art. If the nickel-based catalyst is presulfided or used in the presence of sulfur compounds, the selective hydrogenation has to be carried out at higher temperature, which results in an inferior recovery of the 1,3-butadiene and faster catalyst deactivation. However, as discussed below, sulfur impurities usually found in the hydrocarbon feed streams are not a serious problem to the present unsulfided Ni catalyst in the present process.

The optimum metal loading on the Ni-based and Pd-based catalysts are quite different. The palladium-based catalysts are more active than the nickel-based catalysts based on the active metal content loaded on the catalyst, because the nickel content on a Ni-based catalyst is usually about two orders of magnitude higher than the palladium content on a Pd-based catalyst. However, the unsulfided nickel-based catalyst has superior activity over the palladium-based catalyst based on a given weight of the catalyst or a given volume of the catalyst under a similar hydrogenation condition.

The poisoning effects of organic sulfur compounds, such as mercaptans and heavy metals such as organo-mercuric compounds for the catalysts, such as palladium, copper and copper-zinc-silver-palladium containing catalysts are eliminated in the first unsulfided Ni catalytic reaction zone. Also partial conversion of acetylenic compounds, especially vinyl acetylene, is another objective of the first catalytic reaction zone to reduce the loss and migration of palladium metal and the rate of the build-up of poisonous carbonaceous materials on the catalysts in the second and third catalytic reaction zones. In the case of the use of a copper-based catalyst in the second catalytic zone, the service of the first unsulfided Ni-based catalytic reaction zone prolongs the cycle time of the copper-based catalysts. To accomplish all of these objectives, a part of the unsulfided Ni catalyst in the first catalytic reaction zone is sacrificed as a guard bed. The unsulfided Ni catalyst is present on the support in amounts in excess of that necessary for the selective hydrogenation, thus allowing for some of the nickel to be contaminated with the sulfur or other impurities. The unsulfided Ni is preferably used in an amount of at least 5%, preferably at least 10%, more than required for the selective hydrogenation in question. The advantages of this invention over the current conventional palladium or copper-based catalyst processes are multi folds; faster selective hydrogenation reaction rate, higher recovery of the useful materials such as mono-olefins, diolefins or both, saving hydrogen, and longer catalyst cycle time or service time or both.

In the present process the $C_4$ acetylenic impurities in a mixed crude butadiene stream are removed completely or to less than 30 ppm combined $C_4$ acetylenes (for example, less than 20 ppm VA and 10 ppm EA) by selective hydrogenation with high recovery of 1,3-butadiene in this invention, which makes the separation of 1,3-butadiene from the mixed stream simpler and cheaper.

The catalysts are placed in one or more catalytic reaction zones, which are part of any physical devices. The examples of such devices, in which chemical reactions related to this invention occur, are one or any combinations of fixed bed reactor, distillation column reactor, solvent extractive distillation column reactor, boiling point reactor, trickle bed reactor, moving bed reactor, ebulating bed reactor, fluidized reactor, stirred tank reactor, and the like.

The activation of the unsulfided Ni-based catalyst is carried out at temperature in a range of about 250° F. to about 1000° F. under the ambient hydrogen pressure to about 600 psi hydrogen pressure for 1 hour to 40 hours.

When a single catalytic reaction zone is used, an unsulfided nickel-based catalyst is employed. Hydrogen is premixed with hydrocarbon feed prior to entering the catalytic reaction zone or introduced to the catalytic reaction zone at multiple positions along the catalytic reaction zone.

When multiple catalytic reaction zones are used, a combination of unsulfided nickel-based catalyst, a Pd promoted Cu—Zn—Ag catalyst and optionally a copper-based catalyst is used. The feed is first passed through the unsulfided nickel-based catalytic reaction zone prior to entering the second catalytic reaction zone composed of either lower activity nickel-based catalyst or one or both of the Pd promoted Cu—Zn—Ag catalyst and a copper-based catalyst. Hydrogen is premixed with hydrocarbon feed prior to entering the catalytic reaction zones or added to the catalytic reaction zones at the multiple positions along the catalytic reaction zones.

The selective hydrogenation of acetylenic compounds generates heat in the catalytic reaction zones resulting in hot spots or an undesirably uneven temperature profile in the catalytic reaction zones. The feed is passed through catalytic reaction zone(s) in gas phase, liquid phase or a mixed phase of gas and liquid. The temperature of selective hydrogenation reaction in the catalytic reaction zones is one of the most important process variables. The main distinction is that the present process using the unsulfided Ni is the lower temperatures used for any given reaction compared to the processes using other catalysts. In general, the temperature in the catalytic reaction zone is in a range of about 50° F. to about 420° F., preferably from about 55° F. to about 380° F. But the temperature is determined by the specific acetylenic compounds to be hydrogenated, the dienes and/or olefins to be recovered, catalyst to be used, and the intended physical phase of the hydrocarbons in a specific catalytic reaction zone. For the $C_2$ or $C_3$ acetylene in mixed $C_2$ or $C_3$ olefinic hydrocarbons, the temperature for the selective hydrogenation is in a range of from about 55° F. to about 380° F. For the $C_4$ acetylenic compounds in a mixed butadiene stream, the temperature is in a range of from about 55° F. to 180° F. For the $C_5$ acetylenic compounds in a mixed $C_5$ diolefinic hydrocarbons stream, the temperature is in a range of from about 60° F. to about 350° F. For heavier acetylenic hydrocarbons than $C_5$ acetylenes in heavier hydrocarbons than $C_5$, the temperature is in a range of from about 65° F. to about 400° F.

The selective hydrogenation over the unsulfided Ni catalysts disclosed in this invention is preferably carried out at low hydrogenation temperature in a range of 50° to about 180° F., more preferably from about 70° to 170° F. for $C_4$ acetylenic compounds in crude butadiene stream. To obtain relatively uniform temperature over the catalytic reaction zone, the selective hydrogenation is preferably carried out in a catalytic distillation reactor or a fixed bed reactor with internal cooling system as heat exchanger or a combination of these two reactor systems.

The concentration of hydrogen in the catalytic reaction zones is another important process variable. The concentration of hydrogen in the catalytic reaction zones depends on a number of factors including the concentration of acetylenic compounds in the incoming feed stream into a specific reaction zone, the specific acetylene compound(s), the intended conversion of acetylenes across a specific catalytic reaction zone, the temperature of a specific catalytic reaction zone, the pressure of the catalytic reaction zone, catalyst in a specific reaction zone, and the specific physical device of the catalytic reaction zone. In general, for Group VIII metals containing catalysts, the minimum amount of hydrogen is no less than 25 mole %, preferably 40 mole %, of the concentration of the total acetylenes in the incoming stream into a specific catalytic reaction zone. But for the catalysts containing no Group VIII metals, the minimum amount of hydrogen concentration is no less than 40 mole %, preferably 60 mole % of the concentration of the total acetylenes in the stream coming into a specific catalytic reaction zone.

The pressure of the catalytic reaction zones is in the range of from about 10 psig to about 500 psig, preferably from about 30 psig to 350 psig. The pressure of a catalytic reaction zone is determined by the following specifics; the specific physical device of a catalytic reaction zone, whether a solvent is used or not, the intended temperature of a selective hydrogenation reaction in a specific catalytic reaction zone, catalyst, and intended phase (gas, liquid or a mixed phase of gas and liquid) of hydrocarbons in the catalytic reaction zone.

The flow rate of the hydrocarbons in a specific reaction zone is determined by the followings: the amount of catalyst, the specific physical device of a catalytic reaction zone, intended conversion of acetylenic compounds across the specific reaction zone, and the concentration of hydrogen, temperature and pressure in a specific catalytic reaction zone.

The steam cracked hydrocarbon streams for the production of olefins and dienes containing acetylenic impurities such as acetylene, methyl acetylene, ethyl acetylene, vinyl acetylene, 2-methyl-1-buten-3-yne or phenyl acetylene are passed through a single catalytic reaction zone or a series of two or three catalytic reaction zones to remove acetylenic impurities. Since the objectives, the concentration of acetylenes, and the compositions of the catalysts in each catalytic reaction zone are different, the optimum concentration of hydrogen in each reaction zone is different. Therefore, the hydrogen concentration in each reaction zone is accordingly adjusted by adding hydrogen or removing hydrogen to/from the incoming feed stream to each catalytic reaction zone. Also the process variables (temperature, pressure, and hydrocarbon flow rate) may be independently adjusted for each catalytic reaction zone for the best performance of the catalyst in each reaction zone. An example of a feed stream for the present process is a crude $C_4$ butadiene stream from a steam cracker. When a single catalytic reaction zone is employed, only unsulfided Ni-based catalyst is used. Optionally a combination of a nickel-based catalyst and a palladium-based catalyst, a nickel-based catalyst and a copper-based catalyst, or a nickel-based catalyst and a palladium promoted copper-based catalyst may be used in a given physical device, where the hydrogenation occurs, with or without adjustment of hydrogen at each catalyst reaction zone. The single catalytic reaction zone may be composed of one, two or three different catalysts. It is important that the crude feed always first passes through an unsulfided nickel-based catalyst bed prior to entering other catalyst beds.

A mixture of a crude $C_4$ butadiene stream from a steam cracker and hydrogen is passed through a single catalytic reaction zone or a series of two or three catalytic reaction zones to remove acetylenic impurities. Crude $C_4$ butadiene streams usually contain methyl acetylene, ethyl acetylene, vinyl acetylene, propadiene, and 1,2-butadiene impurities.

The catalyst in the first catalytic reaction zone is comprised of unsulfided Ni or optionally unsulfided Ni and one or more of the elements among Mo, Re, and Bi supported on a porous support such as alumina, silica, and the like. The preferred Ni content on Ni catalysts is from 3 to about 75 wt. % of total catalyst, preferably from 4 to 60 wt. % Ni. The preferred content on a Ni—Mo catalyst are 5 to 60 wt. % for Ni, preferably from 5 to 45 wt. % Ni, and 1 to 40 wt. % for Mo. Alternatively, the catalyst in the first catalytic reaction zone may be composed of two different catalysts of a Ni catalyst and a multi component Ni catalyst discussed above. The two different catalysts may be mixed together prior to loading in the first catalytic reaction zone or alternatively the Ni only catalyst in the front of the other catalyst or vice versa. The poisoning effect of sulfur compounds in the feed stream on the catalysts in the second and third catalytic reaction zones is neutralized in this first catalytic reaction zone by both conversion to organic thioethers and reaction with the Ni catalysts. Other important objectives of the first catalytic reaction zone are partial conversion of acetylenic compounds, especially vinyl acetylene, in the feed stream to minimize the Pd loss/migration (if Pd is used in a subsequent catalyst) and reducing the build-up rate of the carbonaceous materials on the catalyst(s) in the next catalytic reaction zone(s). The recovery of 1,3-butadiene from the first catalytic reaction zone is preferably maintained at higher than about 97 wt. %, preferentially about 98 wt. %. The recovery of 1,3-butadiene, vinyl acetylene or ethyl acetylene is determined as follows:

$$\text{Recovery of } X (\%) = 100 - (N_F - N_P) \times 100/N_F$$

$N_F$=wt. % of X in feed stream, $N_P$=wt. % of X in product stream; where X is 1,3-butadiene, vinyl acetylene or ethyl acetylene.

Since vinyl acetylene can be converted to 1,3-BD by hydrogenation, the recovery of 1,3-BD is mathematically possible to be larger than 100%, which means that the recovery will be higher than 100%, if there is no hydrogenation of 1,3-BD. The concentration of combined acetylenic impurities in the product stream from the first unsulfided Ni-based catalytic reaction zone is in a range from about 20 wt. ppm to about 5000 wt. ppm depending on the concentration of acetylenic impurities in the feed stream. It is possible to completely convert all the acetylenic impurities in the feed stream by passing through a single catalytic reaction zone in the presence of a nickel-based catalyst only. But the loss of various olefins such as 1,3-butadienes, butenes, propylene and ethylene due to over hydrogenation may be too high to justify economically in commercial operation. Also, the first catalytic reaction zone serves to maximize the isomerization of propadiene to methyl acetylene and 1,2-butadiene to 1,3-butadiene.

The product stream from the first catalytic reaction zone may be passed through a second catalytic reaction zone with or without an adjustment for optimal hydrogen concentration at an optimal process condition. In the product stream from the second catalytic reaction zone, the concentration of the combined $C_4$ acetylenic impurities is in a range from 0 wt. ppm to about 350 wt. ppm, depending on the concentrations of acetylenic impurities in the original feed stream to the first catalytic reaction zone and the process condition of the second catalytic reaction zone. The recovery of 1,3-butadiene across the second catalytic reaction zone is better than about 98 wt. %. The catalyst in the second catalytic reaction zone is any one of the conventional palladium-based catalysts or preferably an improved copper catalyst containing at least one Group VIII metal component, a Ag, Au component or mixtures thereof on an alumina support comprising at least one of the properties of average pore diameter larger than 200 Å or apparent bulk density of less than about 0.70 g/cm3, such as a catalyst comprised of Cu, Zn, and optionally Ag supported on porous support such as alumina or a Pd promoted Cu—Zn—Ag disclosed in U.S. Ser. No. 09/827,411, filed Apr. 06, 2001, which is incorporated herein in its entirety. Optionally an improved multi component palladium catalyst comprising Pd, or Pd and other Group 8 metals and at least two metals selected from Ag, Zn or Bi, disclosed in U.S. Ser. No. 09/977,666, filed Oct. 15, 2001, which is incorporated herein in its entirety, may be used in the second catalytic reaction zone. The palladium and nickel contents in the promoted copper catalysts are from about 20 wt. ppm to 0.3 wt. % for Pd and 0 to 15 wt. % for Ni. The copper content is from about 0.4 to 30 wt. %. Silver or gold content is from 0 to about 5 wt. %. Zinc content is from 0 to 25 wt. %. The use of any conventional palladium-based catalyst or conventional copper-based catalyst in the second or subsequent catalytic reaction zone is within the scope of this invention.

A third catalytic reaction zone is optional. The product stream from the second catalytic reaction zone is passed through the third catalytic reaction zone with or without an adjustment for optimal hydrogen concentration at an optimal process condition. In this catalytic reaction zone, the remaining $C_4$ acetylenic impurities are removed completely. Therefore, the product stream from the third catalytic reaction zone contains no detectable $C_4$ acetylenic impurities. The recovery of 1,3-butadiene across the third catalytic reaction zone is better than about 99 wt. %. The catalyst in the third catalytic reaction zone is the improved Cu—Zn—Ag catalyst or the Cu—Zn—Ag catalyst promoted with Pd as described above or optionally unsulfided Ni or both or a conventional copper catalyst as disclosed in U.S. Pat. Nos. 4,440,956 and 4,494,906. The palladium or nickel content in the promoted copper catalyst in this third catalytic reaction zone is from 10 wt. ppm to 0.3 wt. % Pd and 0.1 to about 10 wt. % Ni. The copper content is from about 0.3 to 10 wt. %. Silver and gold content is from 0 wt. % to about 1 wt. %. Zinc content is from 0 to 10 wt. %.

Any combination of the two or three catalysts may be loaded in a single reactor in any form or operational mode. But the feed must be passed first through the unsulfided Ni-based catalytic reaction zone. Optionally the first two reaction zones may be combined into a single reactor by loading the first two catalysts together in series, and optionally a second separate reactor may serve as the third catalytic reaction zone. Another option is combining the last two reaction zones into a single reactor by loading the last two catalysts together in series. Still another option is that three separate reactors serve as three reaction zones. The selective hydrogenation of acetylenic impurities can be carried out in various configurations for the reaction zone. Carrying out the reaction in any combination of modes such as fixed bed reactor, catalytic distillation reactor, solvent extractive catalytic distillation reactor, boiling point reactor, moving bed reactor, fluidized reactor, and the like is a part of this invention. The examples of such combinations are a single fixed bed, a single catalytic distillation column reactor, a single catalytic extractive distillation reactor, three fixed beds, two fixed beds, a catalytic distillation reactor for the first catalytic reaction zone with one or two fixed bed reactors for second and third catalytic reaction zones, one or two fixed bed reactors with a catalytic distillation column reactor for the last catalytic reaction zone, fixed bed reactor for the first reaction zone with a solvent extractive catalytic distillation column reactor for the second reaction zone.

The performance of any catalyst deteriorates with onstream time due to various reasons. One of the reasons is slow build-up of poisonous carbonaceous materials on the catalyst surface. To prolong the catalyst cycle or service time, a solvent may be used to wash off heavy polymers to slow down the build-up rate of the poisonous carbonaceous materials on the catalyst. Therefore, heavy polymers should be soluble, at least to some degree, in the solvent under the selective hydrogenation condition. The examples of such solvent is $C_4$-$C_{10}$ paraffinic hydrocarbons, cyclohexane, methyl cyclohexane, benzene, toluene, alkyl nitrites, furfural, dimethyl acetamide, dimethyl formamide, methylpyrrolidone, formylmorpholine, and ethers such as tetrahydrofuran. Optionally the solvent may be build up in the catalytic distillation system, at the start-up of the unit, by recycling heavy components, which is usually a small part of feed and is also produced by oligomerization and polymerization during the selective hydrogenation in the reactors. One may hydro-treat the heavy component prior to recycle to the top of the catalytic distillation column for more effective removal of heavy polymers on the catalyst. A similar operation can be implemented for the fixed bed system by using a separator to separate heavy components in the reactor effluent or in the feed. Solvent is co-fed with feed to the catalytic reaction zone for the fixed bed operation. For the catalytic distillation or extractive catalytic distillation operation, solvent is introduced at a proper position of the top half of the column. Another alternative operational procedure is occasional washing the catalysts with solvent at a proper temperature in a range from 50° F. to 750° F. under a pressure from 0 to 500 psi, preferably in the presence of hydrogen.

The catalysts useful in this invention can be prepared by depositing catalyst components on supports such as alumina, silica, carbons, charcoal, ceramic materials, polymers, and various structured materials such as packing materials for fixed bed reactors or distillation columns. Preferably the support has surface area of greater than 40 $m^2/g$ for the unsulfided Ni catalysts. Various deposition techniques such as impregnation, spraying, spray drying of slurry, vapor deposition, and the like can be used. All these techniques are well known to those skilled in the arts. Optionally the catalysts can be a structured packing material made out of Ni, Cu, Pd—Cu—Ag alloy, Ni—Pd alloy, Ni—Cu alloy and the like, which can be placed in the selective hydrogen reaction zone in any physical device.

To deposit the components of the catalysts on the shaped supports, the use of one or more of various deposition techniques impregnates inorganic or organic metal compounds on the shaped supports such as spheres, extrudates, tablets, and the like. Usually inorganic salts deposited on supports such as alumina are decomposed to metal oxides by calcining the impregnation products at elevated temperature in air. The metal oxides on the support are reduced to metals to activate the catalysts by using reducing agents such as hydrogen, carbon monoxide, ammonia, methanol, and the like at a suitable temperature. If the catalysts need activation at low temperature, low temperature reducing agents such as hydrazine, aluminum alkyls, formaldehyde, and the like are used. For example, the improved Cu—Zn—Ag catalyst disclosed in Ser. No. 09/827,411, noted above is prepared by impregnating an aqueous mixed solution of copper, zinc and silver nitrate salts on a suitably shaped gamma-alumina in a rotary impregnator followed by drying and calcination at elevated temperature. The palladium promoted Cu—Zn—Ag catalyst is prepared by depositing copper, zinc, silver and palladium on a suitably shaped support such as high temperature calcined porous transition alumina.

Another technique frequently used is that catalytic metal components are precipitated from mixed solutions in the presence or absence of a supporting material and the precipitates are washed with clean water followed by drying to obtain powders which are used to shape various forms by using various techniques such as extrusion, pressing into tablets in proper size and molding. The shaped materials are normally calcined at suitable temperatures. If one needs the catalysts in the small micro sphere form for the fluidized reactor operation, slurries are prepared from the precipitates. The slurries are spray-dried to proper particle size followed by calcination at elevated temperatures. Spray-dried materials can also be shaped to produce catalysts in extrudate or tablet form. Alternatively, the catalysts can be prepared by the catalyst preparation technique disclosed in U.S. Pat. No. 6,337,300. The alloy catalyst is prepared by removing an extractable metal component from a shaped alloy catalyst.

In the following examples the nickel catalysts are all unsulfided metal.

EXAMPLE 1A

Comparative Process

Figure 2:
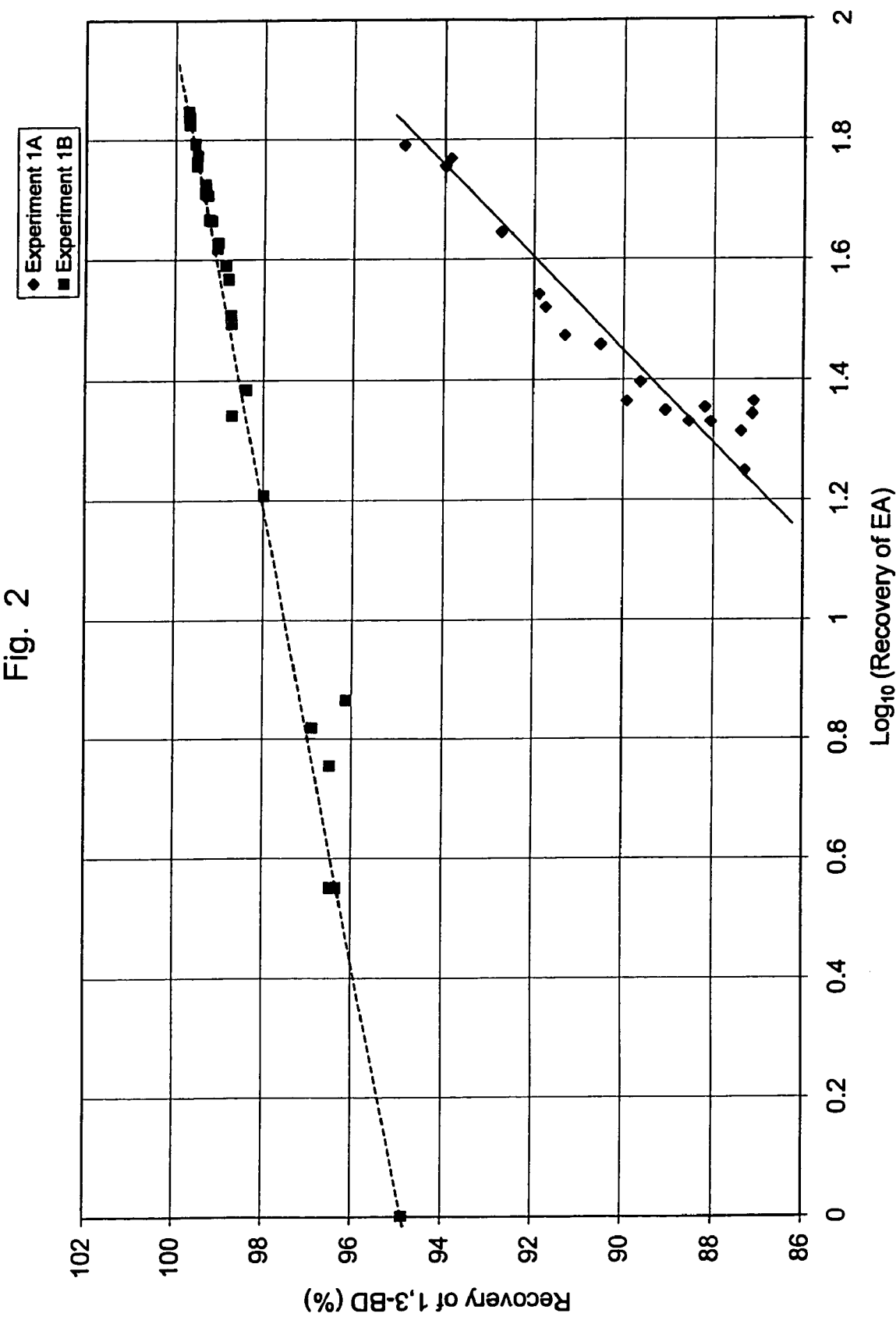
FIG. 2 is a chart comparing Examples 1A and 1B for ethyl acetylene removal.

Commercial eggshell type Pd—Ag catalyst (0.2 wt. % Pd and 0.1 wt. % Ag) supported on α-alumina (G681 obtained from UCI) was used to remove $C_4$ acetylenic impurities in a crude cracked butadiene stream by selective hydrogenation. 50 grams of the catalyst was mixed with 100 ml of 3 mm diameter glass balls and loaded in a vertically mounted up-flow stainless fixed bed reactor (1 inch diameter×20 inch long). The average size of the catalyst is 2.5 mm diameter×6 mm long extrudate. Two thermocouples at each end of catalyst zone are installed to control the reactor temperature. The catalyst was activated at 235° F. by passing 300 cc per min of 33 volume % hydrogen gas in nitrogen for 2.5 hours and then 300 cc per min of hydrogen at 400° F. for 2 hours under 15 psig pressure. The reactor was cooled to ambient temperature. The selective hydrogenation of acetylenic impurities was carried out at 6 ml/min of hydrocarbon feed and at 165 sccm/min of hydrogen flow rate at the beginning of the reaction down to 100 sccm/min toward to the end of the run under 108 psig total reactor pressure. The feed was comprised of 0.95 wt. % vinyl acetylene, 0.14 wt. % ethyl acetylene and 0.20 wt. % methyl acetylene, 72.11 wt. % 1,3-BD, 0.12 wt. % 1,2-BD, 14.61 wt. % butenes and the balance mostly inerts. Because of exothermic heat of hydrogenation, the temperature at the end of the catalyst bed was higher than at the beginning of the catalyst bed. The temperatures of the hydrogenation were 120° to 128° F. at the end of the catalyst bed and 90° F. at the beginning of the catalyst bed. The best quality product from this experiment contained 114 ppm VA and 230 ppm EA at 87.3% recovery of 1,3-butadiene. The result is illustrated in FIGS. 1 and 2.

EXAMPLE 1B

Invention

Fifty grams of HTC-400 (16 wt. % Ni on alumina) obtained from Synethix mixed with 100 ml of 3 mm diameter glass balls and were loaded in a vertically mounted up-flow stainless fixed bed reactor (1 inch diameter ×20 inch long). The catalyst was obtained in activated and then pacified form. The diameter of the catalyst is 1.2 mm diameter trilope extrudates. Two thermocouples at each end of catalyst zone are installed to control the reactor temperature. The catalyst was activated at 235° F. by passing 300 cc per mm of 33 volume % hydrogen gas in nitrogen for 3 hours and then 300 cc per mm of hydrogen at 575° F. for 3 hours under 15 psig pressure. The reactor was cooled to ambient temperature. The selective hydrogenation of acetylenic impurities in the same feed used in the Example 1A was carried out at 6 ml/min of hydrocarbon feed and at 100 sccm/min of hydrogen flow rate at the beginning of the reaction down to 38 sccm/min toward to the end of the run under 108 psig total reactor pressure. The feed was the same feed used in the Example 1A. Because of exothermic heat of hydrogenation, the temperature at the end of the catalyst bed was higher than at the beginning of the catalyst bed. The temperatures of the hydrogenation were 120° F. to 124° F. at the end of the catalyst bed and 77° F. to 84° F. at the beginning of the catalyst bed. The best quality product from this experiment contained 0 ppm for both VA and EA at 94.9% recovery of 1,3-butadiene. The result is illustrated in FIGS. 1 and 2.

The comparison of the results as shown in FIGS. 1 and 2 of the above two experiments indicate a superior performance of the unsulfided Ni catalyst to the palladium-based catalyst.

EXAMPLE 2

Figure 3:
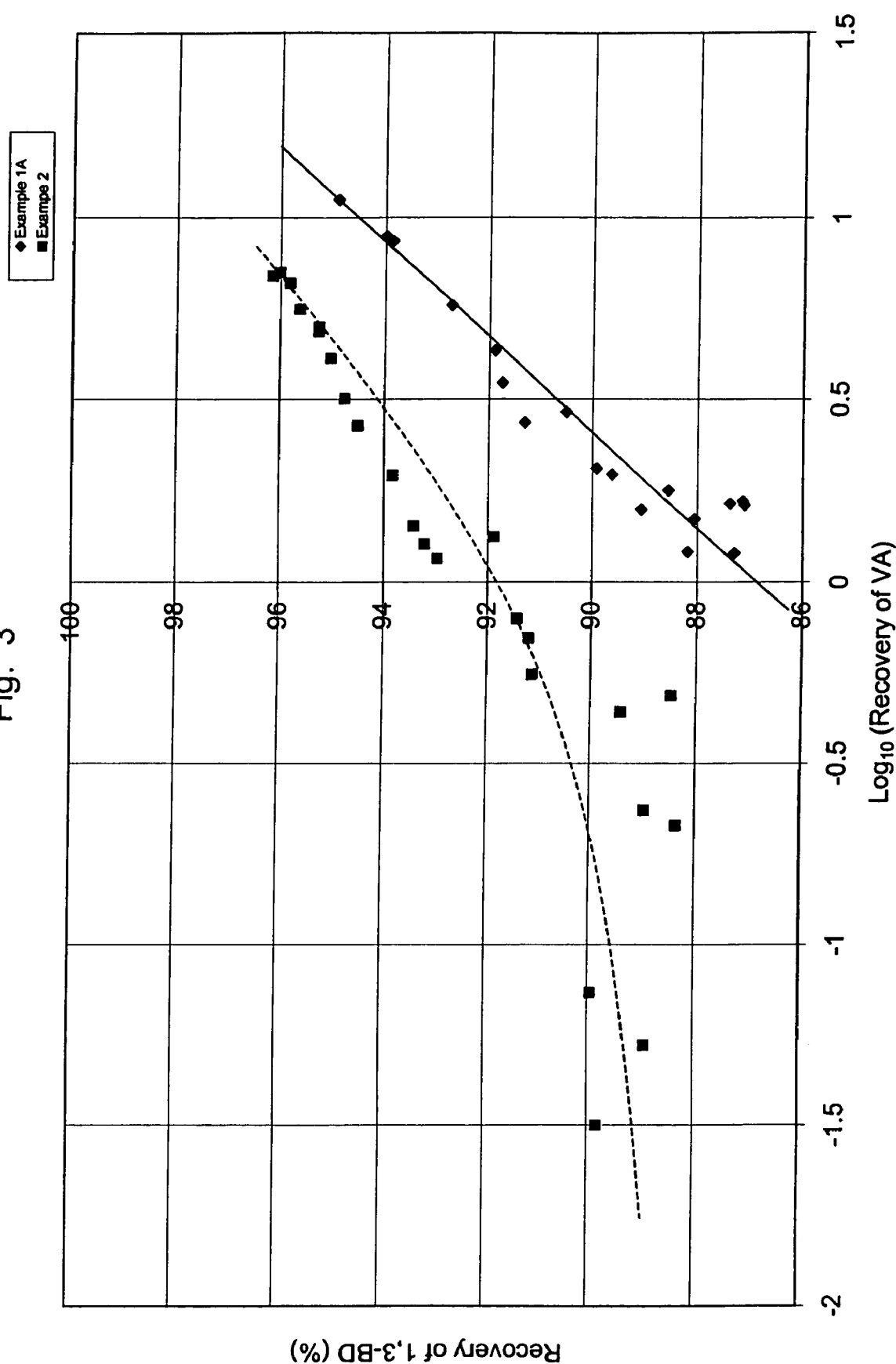
FIG. 3 is a chart comparing Examples 1A and 2 for vinyl acetylene removal.
Figure 4:
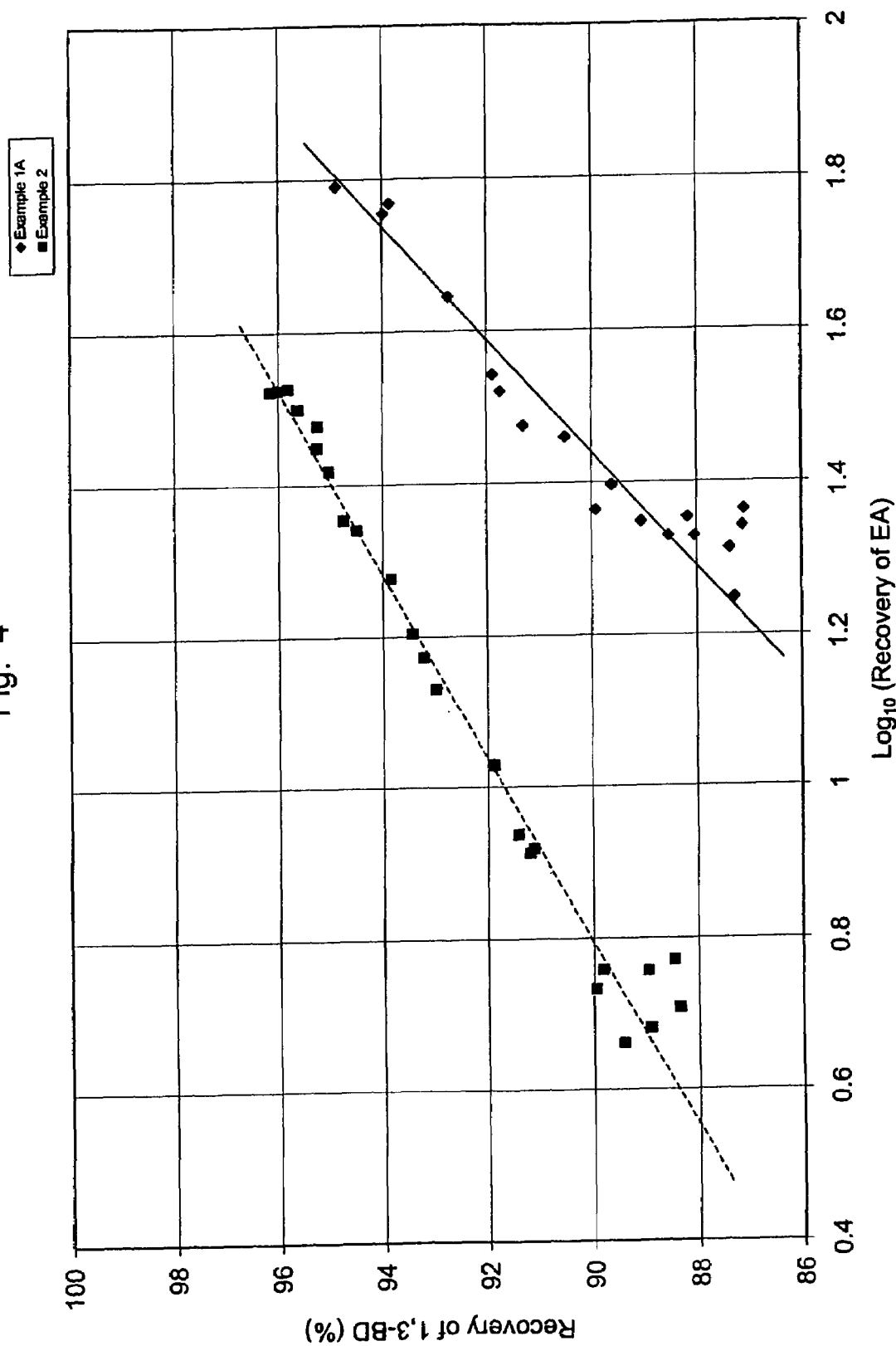
FIG. 4 is a chart comparing Examples 1A and 1B for ethyl acetylene removal.

In this example, the selective hydrogenation of $C_4$ acetylenes with a dual reactor system in series is demonstrated. Fifty grams of HTC-400 (16 wt. % Ni on alumina) were loaded in the first fixed bed reactor and activated in the same manner as described in the Example 1B. Forty grams of the commercial eggshell type Pd—Ag catalyst (G681) used in the Example 1A are loaded in the second fixed bed reactor (1 inch diameter×20 inch long) after mixing with 100 ml of 3 mm diameter glass balls and activated in the same manner as the Example 1A. The feed was the same feed used in the Example 1A. The selective hydrogenation of acetylenic impurities in the feed was carried out at 6 ml/min of hydrocarbon feed to the first reactor and at a constant hydrogen flow rate of 42 sccm/min until the end of this experiment under 108 psig total reactor pressure. The reactor effluent from this first reactor was directly fed to the second reactor. But the reactor effluent was mixed with hydrogen gas at various rates from 100 down to 50 sccm/min prior to entering to the catalytic reaction zone of the second reactor. The temperature of the first hydrogenation reactor was about 120° F. at the end of the catalyst bed and about 84° F. at the beginning of the catalyst bed. The temperature of the second hydrogenation reactor was about 120° to 125° F. at the end of the catalyst bed and about 85° F. at the beginning of the catalyst bed. The reaction products from the second reactor were analyzed to evaluate the performance of the dual reactor system. The results are illustrated in FIGS. 3 and 4 and demonstrate a superior performance of the dual catalyst systems comprised of Ni catalyst and palladium-based catalyst to palladium-based catalyst alone in the Example 1A.

EXAMPLE 3

Figure 6:
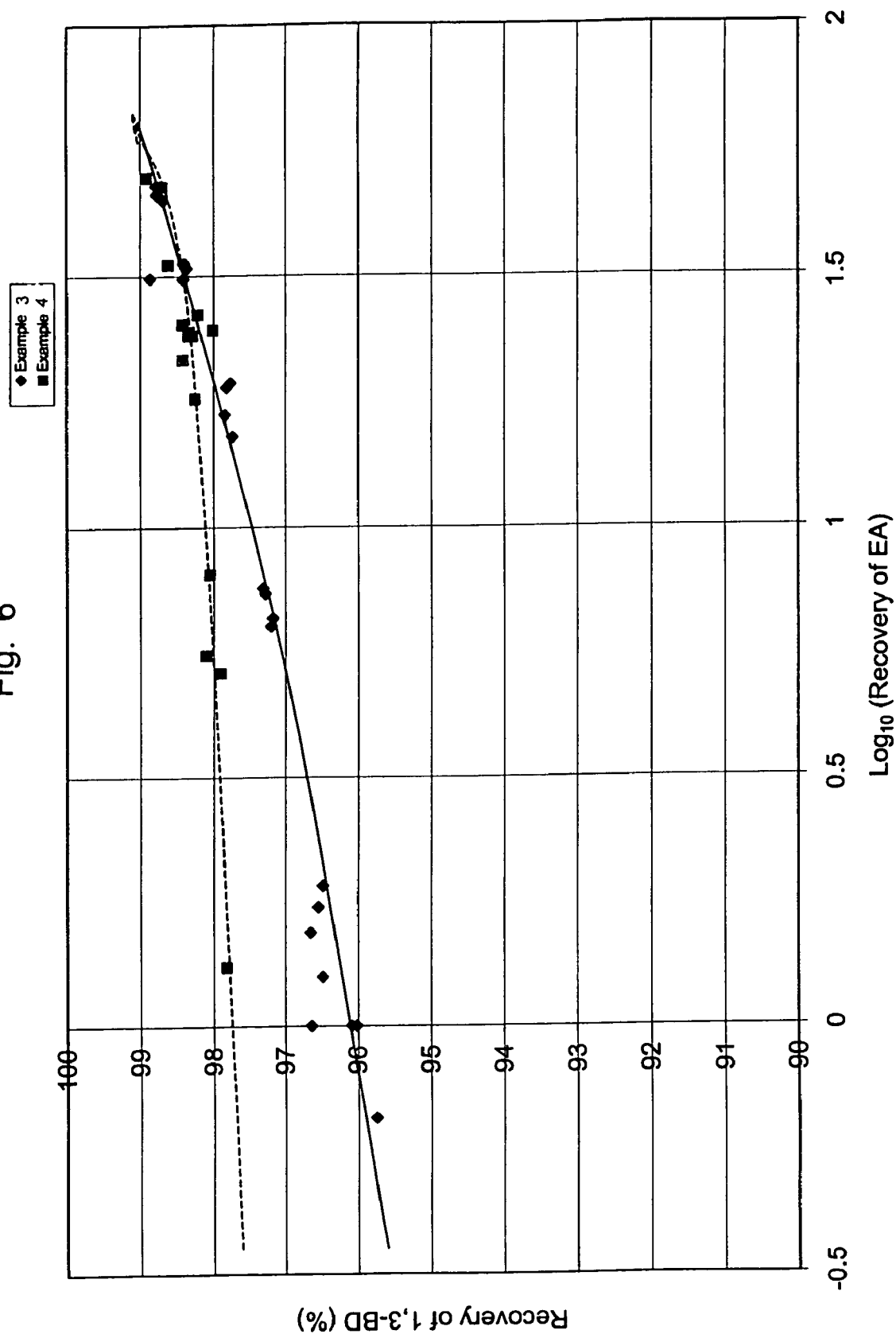
FIG. 6 is a chart comparing Examples 3 and 4 for ethyl acetylene removal.

Fifty grams of a Ni catalyst (28 wt. % Ni; KL6564) obtained from CRI were loaded in a fixed bed reactor in the same manner as described in the Example 1B. The catalyst was activated at 250° F. for 2 hours by passing a mixture of 200 sccm/min $N_2$ and 100 sccm/min $N_2$ and then 670° F. for 4 hours with 300 sccm/min $H_2$. The catalyst was 1.2 mm diameter trilope extrudate. The BET surface area of the catalyst was about 120 $m^2/g$. The feed was comprised of 0.98 w % vinyl acetylene, 0.12 wt. % ethyl acetylene and 0.08 wt. % methyl acetylene, 72.52 wt. % 1,3-BD, 0.12 wt. % 1,2-BD, 14.04 wt. % butenes and the balance mostly inerts. The selective hydrogenation of acetylenic impurities in the feed was carried out at 6 ml/min of hydrocarbon feed and at various hydrogen flow rates from 100 to 40 sccm/min and 108 psig total reactor pressure. The temperature of the hydrogenation reactor was about 119° to 127° F. at the end of the catalyst bed and about 90° to 104° F. at the beginning of the catalyst bed. The recovery of 1,3-butadiene of the product containing 5 ppm VA and 0 ppm EA was 96.0%. The results are illustrated in FIG. 6. The performance of this catalyst is superior to that of the Pd-based catalyst in the Example 1A.

EXAMPLE 4

In this example, the selective hydrogenation of $C_4$ acetylenes with a dual reactor system is demonstrated. A Ni catalyst was loaded in the first fixed bed reactor and a Cu—Zn—Ag catalyst promoted with Pd was loaded in the second fixed bed reactor.

The Cu—Zn—Ag catalyst promoted with Pd was prepared according to the invention disclosure in Ser. No. 09/827,411, noted above using alumina (1/16" diameter spherically shaped) prepared by the oil dropping gelation technique. The physical properties of the alumina is summarized in Table 1. The alumina was calcined at 1100° C. for 3 hours in air. This calcined alumina had the following physical properties: 67.4 $m^2/g$ BET surface area, an average pore diameter of 362 Å, and 0.701 cc/g of total $N_2$ pore volume. The apparent bulk densities of aluminas before calcination and after calcination were about 0.48 g/cc and 0.62 g/cc, respectively. More than about 90% of the pores were larger than 100 Å diameter. XRD of the calcined alumina showed mostly theta-alumina with some delta. This calcined alumina is used to prepare catalyst. The Cu—Zn—Ag catalyst promoted with palladium was prepared by using a two-step impregnation technique. The mixed solution was prepared by dissolving 28.8 g $Cu(NO_3)_2.2.5H_2O$, 10 g $Zn(NO_3)_2.6H_2O$ and 0.5 g $AgNO_3$ in 285 ml water. For the first impregnation, the mixed salt solution was poured over 300 g calcined alumina in a rotary impregnator and then dried at about 200° C. by blowing in hot air. The dried product was calcined at 450° C. for 2 hours. The calculated metal composition on the alumina support based on the compounds used was 2.5 wt. % Cu, 0.7 wt. % Zn and 0.1 wt. % Ag. Another mixed solution was prepared by dissolving 2.275 g $Cu(NO_3)_2.2.5H_2O$, 1.895 g $Zn(NO_3)_2.6H_2O$, 0.25 g $AgNO_3$ and 6.95 g palladium nitrate solution (10 wt. % palladium nitrate in 10 wt. % nitric acid solution purchased from Aldrich) in 70 ml water. This mixed solution was sprayed on the first impregnation product in the rotary impregnator by using an atomizer over a period of about 15 minutes and then dried at 200° C. for about 1 hour by blowing in hot air. The product was calcined at 350° C. for 2 hour in air. Most of the metallic components from the second step spray impregnation were deposited in a thin layer of from about 0.04 mm to 0.06 mm. The calculated metal composition on the final product based on the compounds used was 2.72 wt. % Cu, 0.84 wt. % Zn, 0.15 wt. % Ag and 0.10 wt. % Pd.

Figure 5:
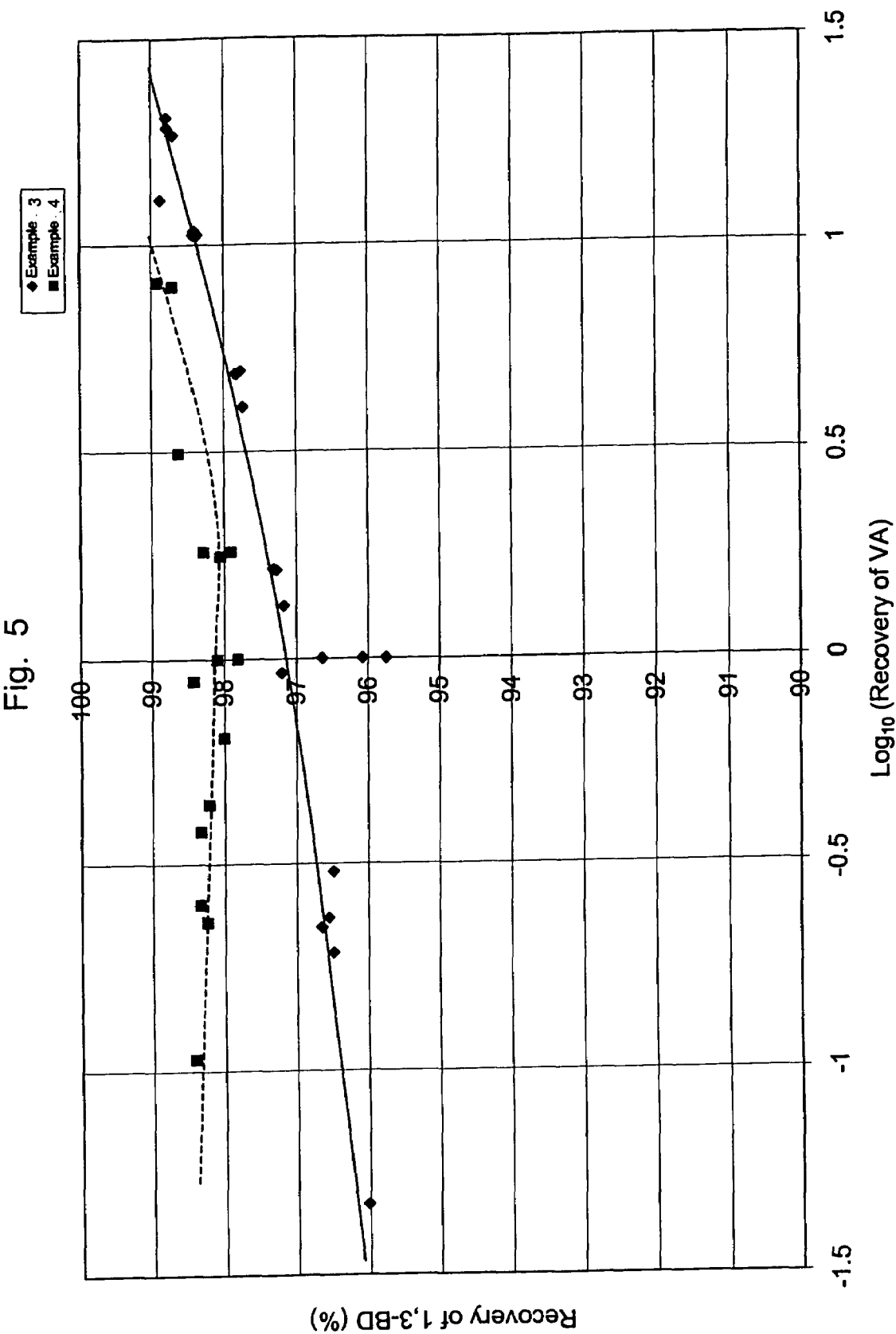
FIG. 5 is a chart comparing Examples 3 and 4 for vinyl acetylene removal.

Fifty grams of the same Ni catalyst (KL6564) in the Example 3 were loaded in the first fixed bed reactor as described in the Example 1B and activated in the same manner as the Example 3. Fifty grams of the Cu—Zn—Ag catalyst promoted with Pd prepared as described above was loaded in the second fixed reactor after mixing 100 ml of 3 mm diameter glass balls and activated at 250° F. for 2 hours by passing a mixture of 200 sccm/min $N_2$ and 100 sccm/min $N_2$ and then 670° F. for 4 hours with 300 sccm/min $H_2$. The feed was comprised of 1.07 wt. % vinyl acetylene, 0.12 wt. % ethyl acetylene and 0.14 wt. % methyl acetylene, 71.89 wt. % 1,3-BD, 0.08 wt. % 1,2-BD, 14.42 wt. % butenes and the balance mostly inerts. The selective hydrogenation of acetylenic impurities in the feed was carried out at 6 ml/min of hydrocarbon feed to the first reactor and at a constant hydrogen flow rate of 40 sccm/min until the end of this experiment under 108 psig total reactor pressure. The reactor effluent from this first reactor was directly fed to the second reactor. But the reactor effluent was mixed with hydrogen gas at various rates from 25 down to 5 sccm/min prior to entering the second catalytic reaction zone. The temperature of the first hydrogenation reactor was about 120° F. at the end of the catalyst bed and about 99° F. to 119° F. at the beginning of the catalyst bed. The temperature of the second hydrogenation reactor was about 115° F. to 123° F. at the end of the catalyst bed and about 80° F. to 85° F. at the beginning of the catalyst bed. The reaction products from the second reactor were analyzed to evaluate the performance of the dual reactor system. The recovery of 1,3-butadiene of the product containing 0 ppm VA and 16 ppm EA was 97.8%. The result is illustrated in FIG. 5 and FIG. 6 to demonstrate a superior performance result of the dual catalyst system comprised of Ni catalyst and the Pd promoted Cu—Zn—Ag catalyst to either the palladium-based catalyst in the Example 1A or the Ni catalyst alone in the Example 3.

TABLE 1

| | |
|---|---|
| ABD, g/cc | 0.48 |
| Single-point BET, $m^2/g$ | 157.5 |
| Multiple-point BET, $m^2/g$ | 170.2 |
| Meso Pore Area, $m^2/g$ | 170.2 |
| Micro Pore Area, $m^2/g$ | 0 |
| Cumulative Adsorption Surface area, $m^2g$ | 172.6 |
| Total Pore Volume (cc/g) for pores less than 493 Å radius at $P/P_0 = 0.9801$ | 0.912 |
| Cumulative Adsorption Pore Volume for pores (20-300 Å radius) | 0.852 |
| Cumulative Desorption Pore Volume for pores (17.5-300 Å radius) | 0.930 |
| Average Pore diameter, Å | 214.4 |

EXAMPLE 5

The selective hydrogenation of $C_4$ acetylenes with a dual reactor system in a series is demonstrated. A Ni catalyst was loaded in the first fixed bed reactor and a Cu—Zn—Ag catalyst promoted with palladium was loaded in the second fixed bed reactor The Cu—Zn—Ag catalyst promoted with Pd was prepared according to U.S. Ser. No. 09/827,411 noted above. The same calcined alumina used in Example 4 was used to prepare the Cu—Zn—Ag catalyst promoted with Pd. The Cu—Zn—Ag—Pd catalyst was prepared by using a two-step impregnation technique. The mixed salt solution was prepared by dissolving 28.8 g $Cu(NO_3)_2.2.5H_2O$, 10 g $Zn(NO_3)_2.6H_2O$ and 0.5 g $AgNO_3$ in 285 ml deionized water. The mixed solution was poured over 300 g calcined alumina in a rotary impregnator and then dried at about 200° C. by blowing in hot air. The dried product was calcined at 450° C. for 2 hours. The calculated metal composition on the alumina support based on the compounds used was 2.53 wt. % Cu, 0.71 wt. % Zn and 0.10% Ag. A mixed salt solution was prepared by dissolving 4.55 g $Cu(NO_3)_2.2.5H_2O$, 3.79 g $Zn(NO_3)_2.6H_2O$, and 1.47 g $AgNO_3$ in 40 g water. A palladium nitrate solution was prepared by dissolving 1.47 g palladium nitrate (42.8% Pd) in 40 g of aqueous 1 wt. % nitric acid solution. The mixed solution and palladium nitrate solution were mixed together. The combined mixed solution was sprayed on the first impregnation product in the rotary impregnator by using an atomizer over a period of about 15 minutes and then dried at 200° C. for about 1 hour by blowing in hot air. The dried product was calcined at 350° C. for 2 hours in air. Most of the metallic components from the second step spray impregnation were deposited in a thin layer of from about 0.12 mm to 0.16 mm. The calculated metal composition on the final product based on the compounds used was 2.91 wt. % Cu, 0.97 wt. % Zn, 0.20% Ag and 0.20 wt. % Pd.

Figure 7:
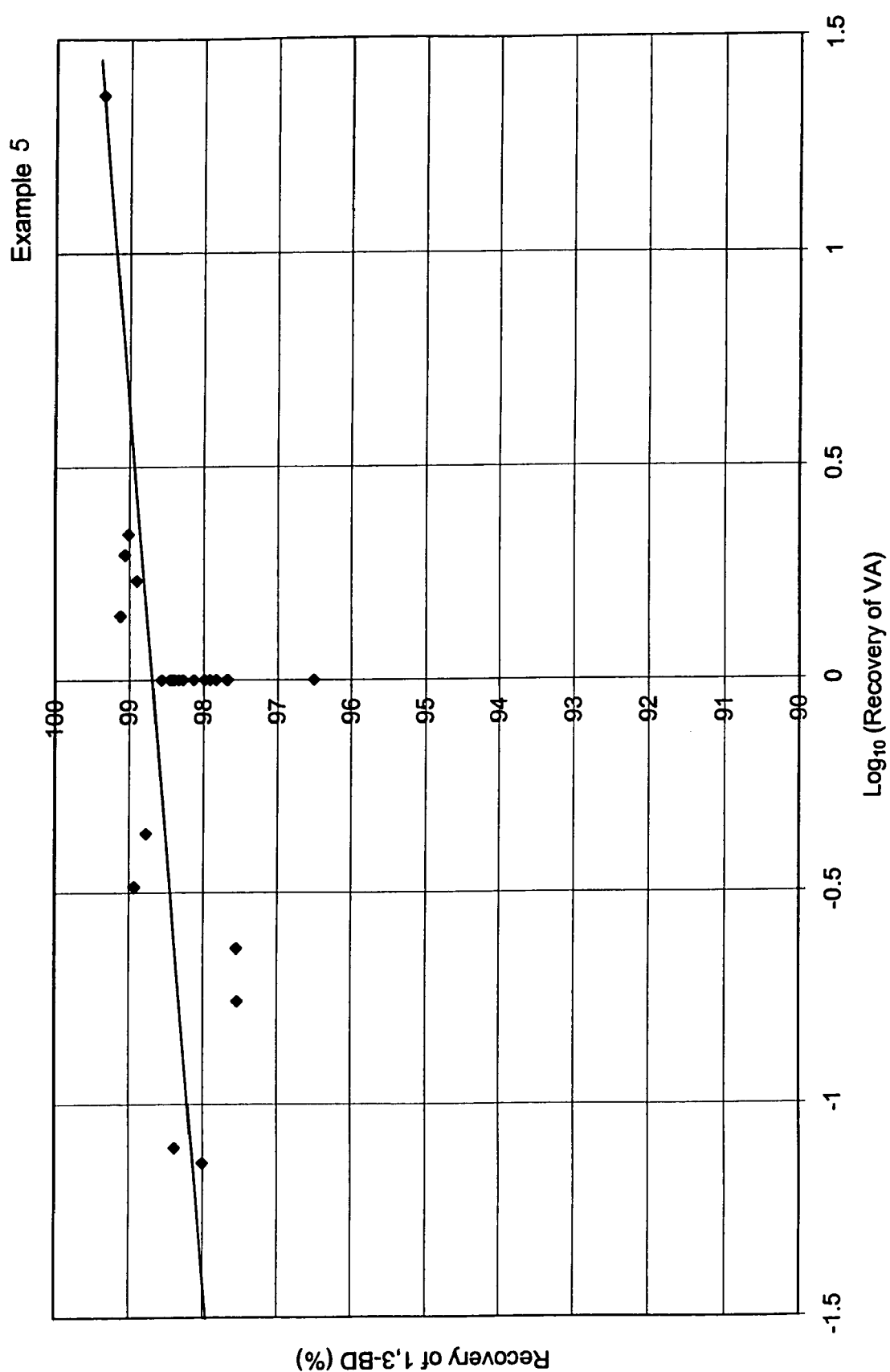
FIG. 7 is a chart showing vinyl acetylene removal for Example 5.
Figure 8:
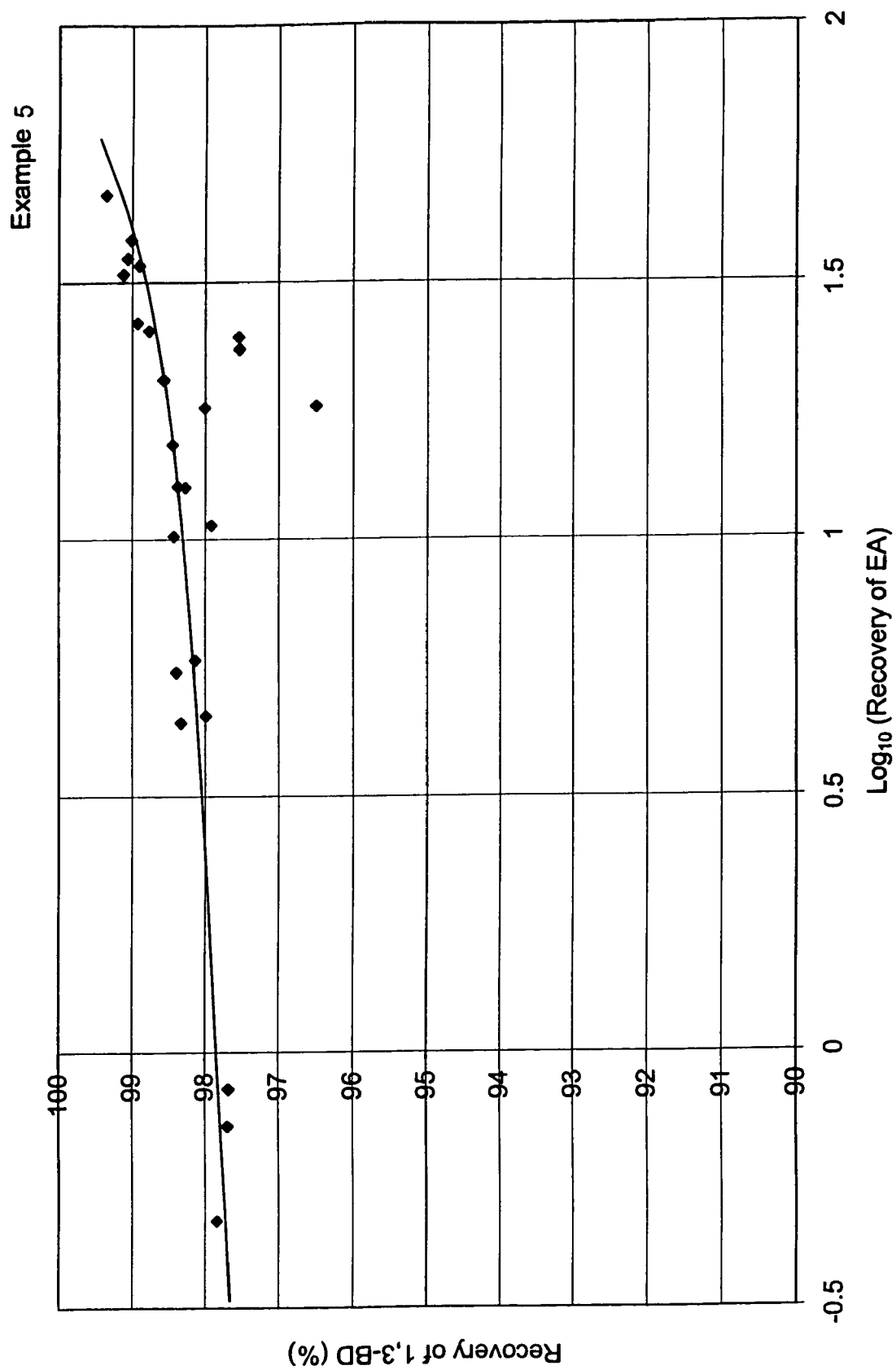
FIG. 8 is a chart showing ethyl acetylene removal for Example 5.

Fifty grams of the same Ni catalyst (KL6564) in the Example 3 were loaded in the first reactor and activated in the same manner as in Example 4. Fifty grams of the Cu—Zn—Ag catalyst promoted with Pd as described above were loaded in the second reactor and activated at 250° F. for 3 hours by passing a mixture of 200 sccm/min $N_2$ and 100 sccm/min $N_2$ and then 575° F. for 3 hours with 300 sccm/min $H_2$ The feed was the same feed used in the Example 3. The selective hydrogenation of acetylenic impurities in the feed was carried out at 6 ml/min of hydrocarbon feed to the first reactor and at a constant hydrogen flow rate of 40 sccm/min until the end of this experiment under 108 psig total reactor pressure. The reactor effluent from this first reactor was directly fed to the second reactor. But the reactor effluent was mixed with hydrogen gas at various rates from 24 down to 6 sccm/min prior to entering to the catalytic reaction zone of the second reactor. The temperature of the first hydrogenation reactor was about 120° F. at the end of the catalyst bed and about 76° F. to 119° F. at the beginning of the catalyst bed. The temperature of the second hydrogenation reactor was about 118° F. to 124° F. at the end of the catalyst bed and about 90° F. to 118° F. at the beginning of the catalyst bed. The reaction products from the second reactor were analyzed to evaluate the performance of the dual reactor system. The recovery of 1,3-butadiene of the product containing 0 ppm VA and 14 ppm EA was 97.5%. The result is illustrated in FIGS. 7 and 8 and demonstrates a superior performance of the dual catalyst system comprised of Ni catalyst and Pd promoted Cu—Zn—Ag catalyst compared to either the palladium-based catalyst in the Example 1A or the Ni catalyst alone in the Example 3.

EXAMPLE 6

Figure 9:
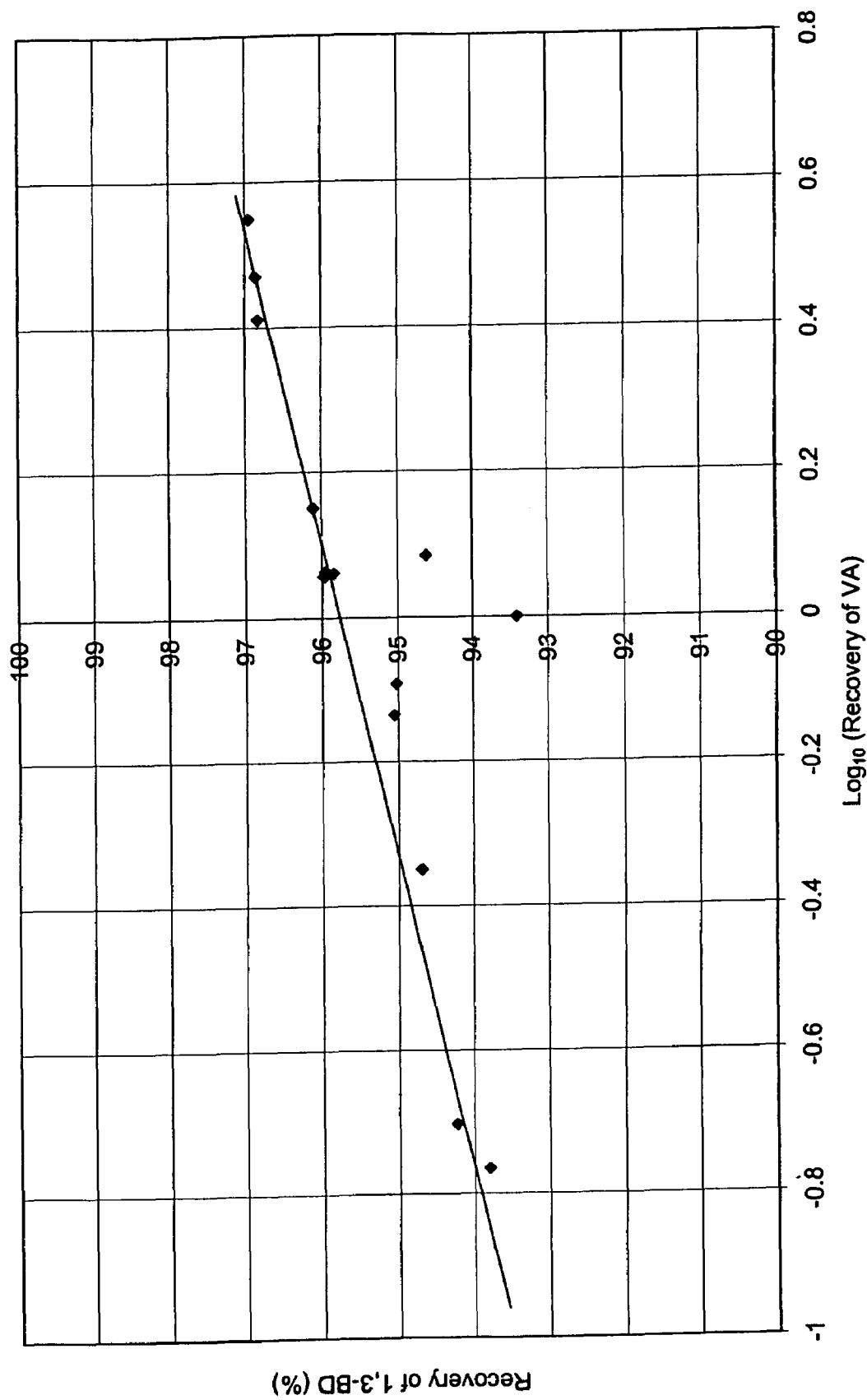
FIG. 9 is a chart showing vinyl acetylene removal for Example 6.
Figure 10:
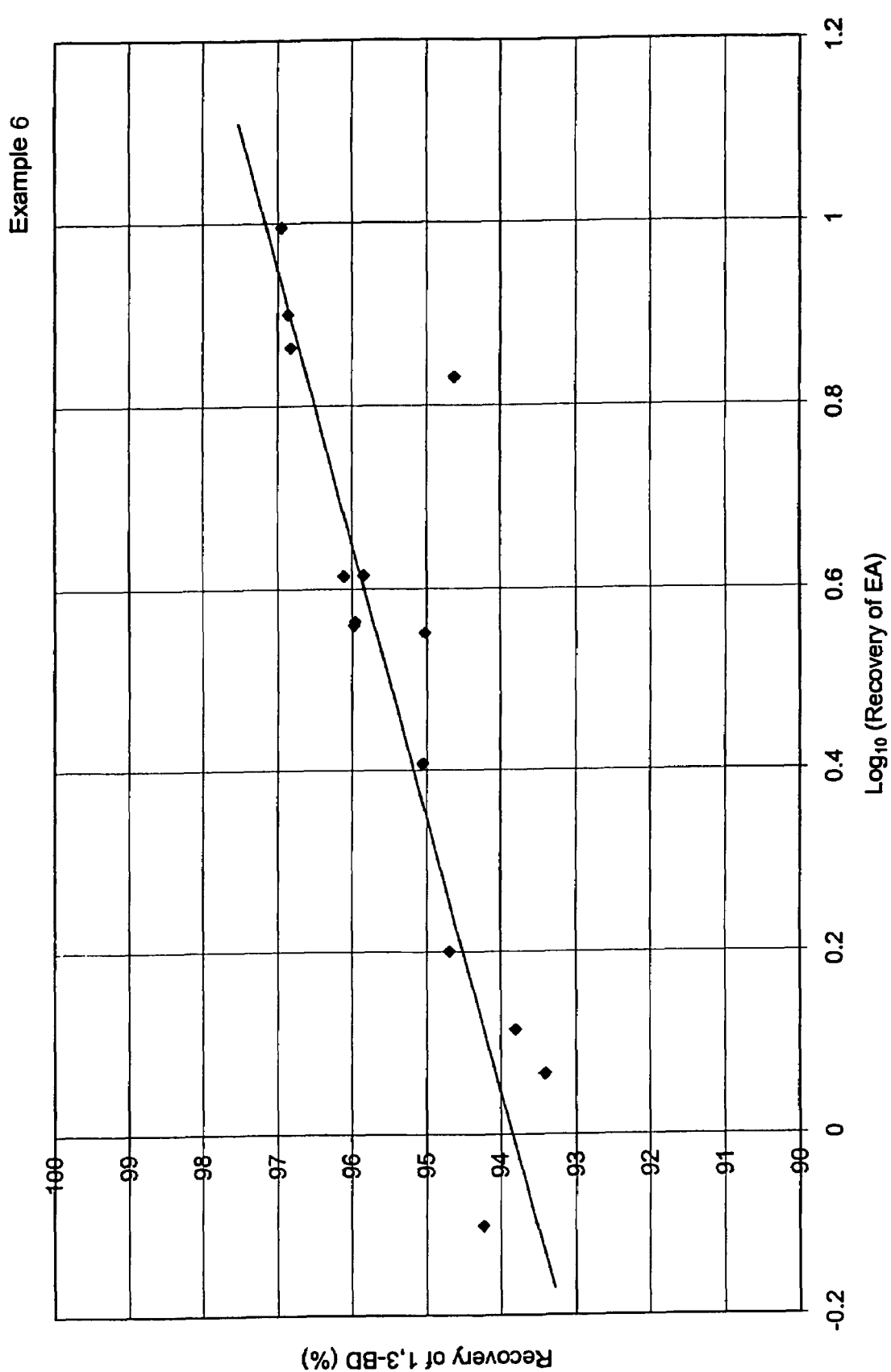
FIG. 10 is a chart showing ethyl acetylene removal for Example 6.

Fifty grams of a Ni catalyst (70 wt. % Ni; KL65271) obtained from CRI were loaded in a fixed bed reactor in the same manner as described in the Example 1B. The catalyst was activated at 250° F. for 3 hours by passing a mixture of 200 sccm/min $N_2$ and 100 sccm/min $N_2$ and then 670° F. for 5 hours with 300 sccm/min $H_2$. The catalyst was 1.2 mm diameter trilope extrudate. The feed was the same feed used in the Example 3. The selective hydrogenation of acetylenic impurities in the feed was carried out at 6 ml/min of hydrocarbon feed and at various hydrogen flow rates of from 105 down to 80 sccm/min and 108 psig total reactor pressure. The temperature of the hydrogenation reactor was about 120° F. to 124° F. at the end of the catalyst bed and about 80° F. at the beginning of the catalyst bed. The recovery of 1,3-butadiene product containing 0 ppm VA and 14 ppm EA was 93.4%. The result is illustrated in FIGS. 9 and 10. The performance of this catalyst is superior to that of the Pd-based catalyst in the Example 1A.

The invention claimed:

1. A process for the reduction of acetylenic compounds in hydrocarbon streams, the process comprising:
   contacting a $C_{3+}$ diene-rich hydrocarbon feed containing a first concentration of acetylenic compounds with a first catalyst in the presence of hydrogen in a first reaction zone to produce a first diene-rich hydrocarbon fraction having a second concentration of acetylenic compounds lower than the first concentration;

contacting the first diene-rich hydrocarbon fraction with a second catalyst in the presence of hydrogen in a second reaction zone to produce a second diene-rich hydrocarbon fraction having a third concentration of acetylenic compounds lower than the second concentration; and wherein the first catalyst consists of supported unsulfided metallic nickel or consists of metallic nickel modified with metals of Mo, Re, Bi, or mixtures thereof.

2. The process according to claim 1, wherein the second catalyst comprises a nickel-based catalyst having a lower activity than the first catalyst.

3. The process according to claim 1, wherein the second catalyst comprises at least one of a Pd based catalyst and a Cu-based catalyst.

4. The process according to claim 1, wherein the second catalyst comprises a Pd promoted Cu-Zn-Ag catalyst.

5. The process according to claim 1, wherein the second catalyst comprises a Cu-based catalyst.

6. The process according to claim 5, wherein the second catalyst comprises a copper catalyst containing at least one Group VIII metal, Ag, Au, or mixtures thereof, on an alumina support comprising at least one of the properties of average pore diameter lager than 200 Å or an apparent bulk density of less than about 0.70 g/cc.

7. The process according to claim 1, wherein the second catalyst comprises a multi-component Pd catalyst comprising Pd, at least one other Group VIII metal, and at least two metals selected from Ag, Zn, and Bi.

8. The process according to claim 1, further comprising premixing hydrogen with the diene-rich hydrocarbon feed prior to contact with the catalyst in the first reaction zone.

9. The process according to claim 1, further comprising adding hydrogen at multiple positions along the first reaction zone.

10. The process according to claim 1, wherein a recovery of diene from the first catalytic reaction zone is at least 97 weight percent.

11. The process according to claim 1, wherein a recovery of diene from the second reaction zone is at least 98 weight percent.

12. The process according to claim 1, further comprising adjusting a hydrogen composition of the first diene rich hydrocarbon stream prior to contact with the second catalyst.

13. The process according to claim 1, wherein the first and second catalyst zones are in a single reactor.

14. The process according to claim 1, wherein the first and second catalyst zones are in separate reactors.

15. The process according to claim 1, further comprising contacting the second diene-rich hydrocarbon stream with a third catalyst in the presence of hydrogen in a third reaction zone to produce a third diene-rich hydrocarbon fraction having a fourth concentration of acetylenic compounds less than the third concentration.

16. The process according to claim 1, wherein the diene-rich hydrocarbon feed comprises a crude butadiene stream.

17. The process according to claim 1, wherein the diene-rich hydrocarbon feed comprises a $C_5$ diolefinic hydrocarbon stream.

18. The process according to claim 1, wherein the first catalyst comprises at least 10 weight percent nickel.

19. The process according to claim 1, wherein the second diene-rich hydrocarbon stream contains no detectable acetylenic impurities.

* * * * *